United States Patent [19]
Nelson et al.

[11] 3,951,972
[45] Apr. 20, 1976

[54] CONTROL OF SODIUM DICHLOROCYANURATE HYDRATION THROUGH AIRSTREAM FLASH DRYING

[75] Inventors: George D. Nelson, Creve Coeur; Kenneth J. Nissing, St. Charles, both of Mo.

[73] Assignee: Monsanto Company, St. Louis, Mo.

[22] Filed: Mar. 27, 1975

[21] Appl. No.: 562,994

[52] U.S. Cl. ............................................. 260/248 C
[51] Int. Cl.$^2$ ..................................... C07D 251/26
[58] Field of Search ............................... 260/248 C

[56] References Cited
UNITED STATES PATENTS

| | | | |
|---|---|---|---|
| 3,289,312 | 12/1966 | Wenzke et al. | 260/248 |
| 3,294,797 | 12/1966 | Shallenberger et al. | 260/248 |

*Primary Examiner*—John M. Ford
*Attorney, Agent, or Firm*—William H. Duffey

[57] ABSTRACT

The degree of hydration of sodium dichlorocyanurate can be varied by controlling particle temperature during airstream flash drying of wet sodium dichlorocyanurate.

6 Claims, No Drawings

CONTROL OF SODIUM DICHLOROCYANURATE HYDRATION THROUGH AIRSTREAM FLASH DRYING

BACKGROUND OF THE INVENTION

1. Field of the Invention

This invention relates to a novel method of producing hydrates of sodium dichlorocyanurate, including hydrates of sodium dichloroisocyanurate. More particularly, this invention relates to the direct conversion of wet sodium dichlorocyanurate to the hydrated form, i.e., the monohydrate, the dihydrate or approximations thereof.

2. Description of the Prior Art

The alkali metal dichlorocyanurates, sometimes termed alkali metal dichloroisocyanurates, are well known materials which are widely used as a source of available chlorine in sanitizing and bleaching applications. Of these, the sodium salt is the most widely used. It is known to exist in the anhydrous form; as the monohydrate (approximately 7.6% combined water of hydration by weight); and as the dihydrate (14.1% combined water). See, for example, U.S. Pat. No. 3,035,056 issued May 15, 1962; U.S. Pat. No. 3,035,057 issued May 15, 1962; and U.S. Pat. No. 3,294,797 issued Dec. 27, 1966.

It is known to prepare sodium dichlorocyanurate by several different methods. One typical method is to react dichlorocyanuric acid with sodium hydroxide under controlled conditions, thereby producing a slurry which contains sodium dichlorocyanurate dihydrate. The product is then filtered from the slurry and dried to the anhydrous form. Another method of preparing sodium dichlorocyanurate involves the direct chlorination of trisodium isocyanurate in an aqueous medium under controlled conditions, followed by filtration of the product and drying to the anhydrous form. Still another method involves bringing together and reacting trichlorocyanuric acid and trisodium cyanurate in an aqueous medium under controlled conditions to produce an aqueous slurry of sodium dichlorocyanurate dihydrate followed by filtration and drying steps to produce the anhydrous form.

Typically, the sodium dichlorocyanurate dihydrate is filtered or centrifuged to produce a wet cake of sodium dichlorocyanurate dihydrate. The latter material can then be dried by one of several methods known to those skilled in the art to produce a free flowing particulate sodium dichlorocyanurate dihydrate. It is known to then convert the dihydrate form to the anhydrous form by heating it at about 105°C. for about 8 hours in a hot air circulating oven as described in U.S. Pat. No. 3,035,056.

It is well known that the alkali metal dichlorocyanurates, as well as certain other chlorinated dry bleach compounds, when exposed to a flame, spark or other high temperature source, can begin to burn and continue burning after the initial heat source has been removed until all of the material is consumed. This phenomenon is referred to as self-sustaining and self-propagating decomposition. It is further known that the presence of combined water of hydration lessens the tendency toward self-propagating decomposition. Thus, sodium dichlorocyanurate monohydrate is less susceptible to self-propagating decomposition than anhydrous sodium dichlorocyanurate. Sodium dichlorocyanurate dihydrate is in turn even less susceptible than the monohydrate. The presence of bound water of hydration has also been found to relieve dust problems associated with the anhydrous product.

Thus, the advantageous properties of sodium dichlorocyanurate monohydrate and dihydrate make those products attractive for many bleaching, sterilizing, sanitizing and disinfecting applications, notwithstanding an initial loss of available chlorine as compared to the anhydrous product. For example, anhydrous sodium dichlorocyanurate usually contains initially about 63 percent available chlorine as compared to about 59 percent available chlorine in the monohydrate and about 56 percent available chlorine in the dihydrate.

Lack of commercial success for the monohydrate of sodium dichlorocyanurate can be ascribed in part to the difficulty in manufacture. For example, it has been found that the use of oven drying or carrier drying techniques usually result in either the loss of both molecules of bound water or the loss of neither molecule of bound water. Furthermore, production of the monohydrate form of sodium dichlorocyanurate has heretofore involved the use of vacuum drying equipment. In U.S. Pat. No. 3,035,056 there is found an illustration of the dehydration of sodium dichlorocyanurate dihydrate to the monohydrate by "drying at 70°C. under vacuum for about 3 hours."

SUMMARY OF THE INVENTION

The improvement disclosed herein is based upon the unexpected discovery that the monohydrate and the dihydrate of sodium dichlorocyanurate can be prepared economically and efficiently without the need for vacuum (although subatmospheric pressures are permissible) and without many of the difficulties encountered in the prior art.

The principal object of the present invention is to provide a controlled method for continuously producing sodium dichlorocyanurate monohydrate or sodium dichlorocyanurate dihydrate by the direct conversion of wet sodium dichlorocyanurate feed. This object has been accomplished through the use of airstream flash drying (sometimes called pneumatic conveying-type drying) of wet sodium dichlorocyanurate filter cake or centrifuge cake within determined temperature ranges.

DESCRIPTION OF THE INVENTION AND PREFERRED EMBODIMENTS

This invention provides a method for the direct conversion of sodium dichlorocyanurate wet cake to the dihydrate form or the monohydrate form without the use of vacuum drying, the need for large vacuum equipment and the associated operating expenses being thereby eliminated. Numerous other known impediments to efficient monohydrate and dihydrate manufacture are likewise overcome by the process disclosed herein.

In practicing the present invention, sodium dichlorocyanurate wet cake may be prepared by any of several conventional methods such as, for example, by reacting dichlorocyanuric acid with aqueous sodium hydroxide using conditions similar to those described in U.S. Pat. No. 3,294,797. The wet, solid product which is separated from the slurry resulting from the reaction may be directly used in the process of this invention.

In a preferred method, the wet sodium dichlorocyanurate is mixed with previously produced dry sodium dichlorocyanurate monohydrate or dihydrate (as the case may be) to provide a flowable particulate mixture. When used in the present context, "dry" refers to the state of being essentially free of uncombined water and does not refer to the bound water of hydration. The flowable particulate mixture is then contacted with a stream of heated air or gas to maintain the particle temperature within the desired temperature range to remove essentially all of the uncombined water, taking care not to remove either molecule of bound water of hydration, thus resulting in the sodium dichlorocyanurate dihydrate product. In such case, the desired particle temperature range should be from about 55°C. to about 60°C.

If instead, the desired product is sodium dichlorocyanurate monohydrate, the particle temperature range should be controlled between about 70°C. and about 95°C., preferably 75°C. to 85°C., whereby one molecule of bound water of hydration is removed.

The time duration of airstream flash drying in the present process varies according to the desired particle temperature which in turn is dependent upon hot air or hot gas temperature in the stream. In pneumatic conveying dryers such as those which are useful for airstream flash drying according to the present process, the heat transfer is by convection from the conveying gas. Moisture is almost instantaneously removed from wet solid particles by dispersing and conveying them in direct intimate contact with the hot air or hot gas. The characterizing feature of airstream flash drying is the extremely short retention time which can be in the order of 3 to 10 seconds, sometimes even a fraction of 1 second.

With a free-flowing material and primarily surface moisture only, the dryer frequently assumes the form of an airconveying system using heated gas as the conveying medium.

There are four fundamental factors which govern evaporation in a short retention time convection dryer (airstream flash dryer) where the heat is supplied and the moisture transported by air or gases. These are moisture dispersion, temperature differential, particle size and agitation. Such factors are described in detail and typical airstream flash dryers are illustrated on pages 242 through 251 of the ENCYCLOPEDIA OF CHEMICAL PROCESS EQUIPMENT, by William J. Mead, Reinhold Publishing Corporation, New York, N.Y. (1964).

In carrying out the step whereby sodium dichlorocyanurate wet cake is flash dried to the dihydrate or the monohydrate form, whichever is desired, air is the preferred contacting medium although other drying gases may also be utilized to achieve the same result. In this regard, the contact of gas and solid may be carried out using any of the drying apparatus known to those skilled in the art which permits intimate contact of the product particles with the gas for the required time duration. For example, the initial drying or dehydration may be carried out in conjunction with a pneumatic conveying system in a process where the sojourn time within the system prevails for the required period and the particle temperature is controlled within the specified temperature range.

The particle temperature range specified herein for direct conversion of the wet cake to sodium dichlorocyanurate monohydrate (i.e., 70°C. to 95°C.) is important because at temperatures slightly above 95°C., dehydration will proceed to a greater degree than desired which results in the production of anhydrous sodium dichlorocyanurate. Similarly, at particle temperatures slightly below 70°C., dehydration will proceed to a lesser degree than desired such that unwanted, unconverted, sodium dichlorocyanurate dihydrate will result.

The particle temperature range specified herein for the direct conversion of sodium dichlorocyanurate wet cake to the dihydrate form (i.e., 55°C.–60°C.) is likewise important. If the particle temperature during flash drying is allowed to substantially exceed 60°C. there can be an undesirable loss of bound water. At particle temperatures significantly below 55°C., it has been found that the resulting dihydrate product is not satisfactorily dried.

A further understanding of the processes and the advantages of the present invention will be derived from the following Examples which are intended to illustrate the invention but not to limit the scope thereof, parts and percentages being by weight unless otherwise specified.

EXAMPLE 1

This Example illustrates the direct conversion by airstream flash drying of sodium dichlorocyanurate wet cake to the anhydrous form. Wet sodium dichlorocyanurate containing 18 percent moisture was prepared in a manner similar to the teachings of U.S. Pat. No. 3,294,797. A pilot plant airstream flash dryer was set up using a 4.5 meter section of 12.7 mm. inside diameter stainless steel tubing as the dryer tube. The tube was heavily insulated to minimize heat loss through the wall. Air flow was measured with a rotameter prior to heating in an electrical air heater. The air flow was adjusted to a velocity of approximately 1100 meters per minute. Sodium dichlorocyanurate wet cake (3.5 parts) was fed into the dryer just downstream of the air heater with a varible speed screw feeder. The sodium dichlorocyanurate feed for the flash dryer was prepared to simulate the mixing of centrifuge cake from the wet end of the process and recycled, dried anhydrous product. The feed was prepared by mixing 3.5 parts wet sodium dichlorocyanurate containing 18 percent moisture with 6.5 parts of previously dried anhydrous product at 120°C. in a laboratory Hobart mixer to give a composite feed moisture of 6.5 percent. The sodium dichlorocyanurate feed rate to the dryer was adjusted to 50 grams per minute. Inlet air temperature to the dryer was controlled at 300°C. to achieve a particle temperature of 122°C. This, in turn, resulted in a vent air (exit air) temperature of 150°C. Once the desired conditions were reached, the product receiver was changed such that only that product exposed to these particle temperature conditions was collected. The dried product was separated from the airstream by means of a cyclonic separator which discharged into the product receiver. The vent air then passed through a small bag dust collector before discharging to the atmosphere. Thermocouples located just prior to the feed entry point and at the cyclone were adapted to measure inlet and vent temperatures, respectively. The product particle temperature was measured as it discharged into the product receiver. The run was continued for 15 minutes after the desired conditions were reached. The dried product, identified as anhydrous sodium dichlorocyanurate, contained 0.41 percent moisture and 63.6 percent available chlorine.

EXAMPLE 2

This Example illustrates the direct conversion of wet sodium dichlorocyanurate to the dihydrate form by means of airstream flash drying. The pilot plant setup described in Example 1 was used for this illustration. Wet feed for this Example was prepared in order to simulate recycling approximately 60 percent of the desired dihydrate product. This was achieved by mixing 6 parts of recycled material at 13 percent moisture with 4 parts wet material at 18 percent moisture in a laboratory Hobart mixer to give a resulting feed composite having 15 percent moisture. The feed rate was again adjusted to 50 grams per minute. The inlet air temperature was adjusted to produce a particle temperature of 58°C. with a vent temperature of 75°C., which resulted in an inlet air temperature of 118°C. Once the desired conditions were reached, the product receiver was changed so that only the desired dihydrate product at these conditions was collected. The run was continued for 15 minutes after the desired conditions were reached. The dried product, identified as sodium dichlorocyanurate dihydrate, contained 13.3 percent moisture and assayed 55.4 percent available chlorine.

EXAMPLE 3

This Example illustrates the direct conversion of wet sodium dichlorocyanurate to the monohydrate form through airstream flash drying. The pilot plant setup described in Example 1 was used for this illustration. The feed was prepared to simulate a 60 percent recycle by mixing 6 parts of the desired monohydrate product having 8 percent moisture with 4 parts of wet feed material at 18 percent moisture to give a composite feed having 12 percent moisture. Again the feed rate was adjusted to 50 grams per minute. The inlet air temperature was controlled to give a particle temperature in the discharged product of 80°C. with a vent temperature of 93°C. The resulting air inlet temperature was 190°C. Once the desired conditions were reached the product receiver was changed so that only the desired monohydrate product at these conditions was collected. The run was continued for 15 minutes after the desired conditions were reached. The dried product, identified as sodium dichlorocyanurate monohydrate, contained 7.4 percent moisture and assayed 59.2 percent available chlorine.

Examples 2 and 3 above are illustrative of the process of the present invention wherein the degree of hydration of sodium dichlorocyanurate can be controlled by air stream flash drying techniques. Such control is applied by direct conversion of wet sodium dichlorocyanurate feed in the form of centrifuge cake or filter cake. While the retention time of the solid particles in the airstream drying illustrations of Examples 2 to 3 was not precisely determined, it is estimated that such retention time was in the order of 1 second. Actual knowledge of or control of retention time is not vital in successful practice of the present invention so long as the necessary temperature ranges are adhered to during continuous production of the desired hydrated products. Thus, efficient production of sodium dichlorocyanurate dihydrate by the direct conversion of wet cake feed through airstream flash drying requires maintenance of particle temperature in the dryer at about 55°C. to 60°C. Similarly, efficient production of the monohydrate by the same technique necessitates a particle temperature range in the dryer of about 70°C. to about 95°C. It should be understood, of course, that the hydrated product resulting from operation within the respective temperature ranges does not necessarily contain the exact theoretical quantity of bound water of hydration. There will usually be slight variations in the amount of bound water. Nevertheless, observation of the respective operating temperature ranges for the particular material will result in a monohydrate or a dihydrate having, on a nominal basis, the correct combined water of hydration.

While this invention has been described with respect to specific examples and embodiments, it is to be understood that the invention is not limited thereto and that it can be variously practiced within the scope of the following claims.

The embodiments of this invention in which an exclusive property or privilege is claimed are defined as follows:

1. A method for the direct conversion of wet sodium dichlorocyanurate particles to sodium dichlorocyanurate monohydrate which comprises introducing said wet sodium dichlorocyanurate particles to an airstream or gas stream flash dryer and controlling the particle temperature between about 70°C. and about 95°C.

2. A method of claim 1 wherein the particle temperature is controlled between about 75°C. and about 85°C.

3. A method for the continuous direct conversion of wet sodium dichlorocyanurate particles to dry sodium dichlorocyanurate monohydrate which comprises:
   a. mixing recycled dry sodium dichlorocyanurate monohydrate particles with wet sodium dichlorocyanurate feed to provide a wet, flowable, particulate mixture;
   b. introducing said mixture to an airstream or gas stream flash dryer; and
   c. controlling the particle temperature between about 70°C. and about 95°C.

4. A method of claim 3 wherein the particle temperature is controlled between about 75°C. and about 85°C.

5. A method for the direct conversion of wet sodium dichlorocyanurate particles to sodium dichlorocyanurate dihydrate which comprises introducing said wet sodium dichlorocyanurate particles to an airstream or gas stream flash dryer and controlling the particle temperature between about 55°C. and about 60°C.

6. A method for the continuous direct conversion of wet sodium dichlorocyanurate particles to dry sodium dichlorocyanurate dihydrate which comprises:
   a. mixing recycled dry sodium dichlorocyanurate dihydrate particles with wet sodium dichlorocyanurate feed to provide a wet, flowable, particulate mixture;
   b. introducing said mixture to an airstream or gas stream flash dryer; and
   c. controlling the particle temperature between about 55°C. and about 60°C.

* * * * *